United States Patent
Cheung et al.

(10) Patent No.: US 7,038,096 B2
(45) Date of Patent: May 2, 2006

(54) HYDROCARBON HYDROGENATION CATALYST COMPOSITION, A PROCESS OF TREATING SUCH CATALYST COMPOSITION, AND A PROCESS OF USING SUCH CATALYST COMPOSITION

(75) Inventors: Tin-Tack Peter Cheung, Kingwood, TX (US); Joseph J. Bergmeister, Kingwood, TX (US); Marvin M. Johnson, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 37 days.

(21) Appl. No.: 10/819,584

(22) Filed: Apr. 7, 2004

(65) Prior Publication Data

US 2004/0192984 A1    Sep. 30, 2004

Related U.S. Application Data

(62) Division of application No. 09/949,130, filed on Sep. 7, 2001, now Pat. No. 6,734,130.

(51) Int. Cl.
    *C07C 5/02* (2006.01)
(52) U.S. Cl. .................. 585/250; 585/260; 585/277; 585/325; 585/259
(58) Field of Classification Search ............ 585/250, 585/260, 277, 325, 259
    See application file for complete search history.

(56) References Cited

U.S. PATENT DOCUMENTS

| | | | |
|---|---|---|---|
| 2,802,889 A | 8/1957 | Frevel et al. ................ 260/677 |
| 3,325,556 A | 6/1967 | De Rosset et al. .......... 260/677 |
| 3,775,506 A * | 11/1973 | Houston et al. ............. 585/259 |
| 3,935,264 A | 1/1976 | Bhutani ....................... 260/580 |
| 4,372,840 A | 2/1983 | Bearden et al. ............. 208/113 |
| 4,404,124 A | 9/1983 | Johnson et al. ............. 252/466 |
| 4,484,015 A | 11/1984 | Johnson et al. ............. 585/262 |
| 4,517,395 A | 5/1985 | Obenaus et al. ............. 585/259 |
| 4,571,442 A | 2/1986 | Cosyns et al. .............. 585/261 |
| 4,960,647 A | 10/1990 | Grundy .................... 428/472.1 |
| 5,057,206 A | 10/1991 | Engel et al. ................. 208/143 |
| 5,227,407 A | 7/1993 | Kim ............................ 518/700 |
| 5,332,705 A | 7/1994 | Huang et al. ................ 502/53 |
| 5,475,173 A | 12/1995 | Cheung et al. .............. 585/259 |
| 5,488,024 A | 1/1996 | Cheung et al. .............. 502/325 |
| 5,489,565 A | 2/1996 | Cheung et al. .............. 502/325 |
| 5,510,550 A | 4/1996 | Cheung et al. .............. 585/259 |
| 5,516,851 A | 5/1996 | Flick et al. ................ 525/330.2 |
| 5,518,556 A | 5/1996 | Weber et al. ................ 148/430 |
| 5,565,547 A | 10/1996 | Hefner et al. ................ 528/392 |
| 5,583,274 A | 12/1996 | Cheung et al. .............. 585/261 |
| 5,585,318 A | 12/1996 | Johnson et al. ............. 502/330 |
| 5,587,348 A | 12/1996 | Brown et al. ............... 502/230 |
| 5,648,576 A | 7/1997 | Than et al. .................. 585/260 |
| 5,698,752 A | 12/1997 | Brown et al. ............... 585/260 |
| 5,866,735 A | 2/1999 | Cheung et al. .............. 585/273 |
| 5,889,187 A | 3/1999 | Than et al. .................. 585/260 |
| 6,054,409 A | 4/2000 | Thanh et al. ................ 502/330 |
| 6,127,310 A | 10/2000 | Brown et al. ............... 502/339 |
| 6,204,218 B1 | 3/2001 | Flick et al. .................. 502/243 |

FOREIGN PATENT DOCUMENTS

| | | |
|---|---|---|
| DE | 1926503 | 1/1970 |
| DE | 3312252 | 10/1984 |
| EP | 0064301 | 7/1985 |
| EP | 0689872 | 1/1996 |
| EP | 0686615 | 1/2000 |
| GB | 1439489 | 6/1976 |
| JP | 5959634 | * 4/1984 |

OTHER PUBLICATIONS

Park, Yeung H., et al, "Promotional Effects of Potassium on Pd/$Al_2O_3$ Selective Hydrogenation," *American Chemical Society*, 1992, 31, pp. 469-474.
Boitiaux, J-P, et al, "Newest Hydrogenation Catalysts," *Hydrocarbon Processing*, Mar. 1985, pp. 51-59.
International Search Report, PCT/US03/07109; Nov. 27, 2003; 3 pages.

* cited by examiner

*Primary Examiner*—Tam M. Nguyen
(74) *Attorney, Agent, or Firm*—Rodney B. Carroll; K. KaRan Reed; David W. Dockter

(57) ABSTRACT

A process of treating a catalyst composition containing palladium, an inorganic support, and a catalyst component, such as silver and/or a modifier such as alkali metal fluoride, is provided. The process involves contacting a catalyst composition with a first treating agent comprising carbon monoxide under a first treating condition to provide a treated catalyst composition. As an option, such treated catalyst composition can then be contacted with a second treating agent comprising a hydrogen-containing fluid under a second treating condition. The treated catalyst composition can be used in a selective hydrogenation process in which highly unsaturated hydrocarbons such as diolefins and/or alkynes are contacted with such treated catalyst composition in the presence of hydrogen to produce less unsaturated hydrocarbons such as monoolefins.

20 Claims, No Drawings

HYDROCARBON HYDROGENATION CATALYST COMPOSITION, A PROCESS OF TREATING SUCH CATALYST COMPOSITION, AND A PROCESS OF USING SUCH CATALYST COMPOSITION

CROSS-REFERENCE TO RELATED APPLICATIONS

This is a divisional application of U.S. patent application Ser. No. 09/949,130, filed Sep. 7, 2001 now U.S. Pat. No. 6,734,130, issued May 11, 2004 and entitled "Hydrocarbon Hydrogenation Catalyst Composition, A Process Of Treating Such Catalyst Composition, And A Process Of Using Such Catalyst Composition," which patent application is hereby incorporated herein by reference.

BACKGROUND OF THE INVENTION

This invention relates to a hydrocarbon hydrogenation catalyst composition, a process of treating a hydrogenation catalyst composition, and to a hydrogenation process employing such hydrogenation catalyst composition.

It is known to one skilled in the art that a less unsaturated hydrocarbon compound can be produced by a thermal cracking process. For example, a fluid stream containing a saturated hydrocarbon such as, for example, ethane, propane, butane, pentane, naphtha, and the like and combinations thereof can be fed into a thermal (or pyrolytic) cracking furnace. Within the furnace, the saturated hydrocarbon is converted to an unsaturated hydrocarbon compound such as, for example, ethylene or propylene. Such unsaturated hydrocarbons are an important class of chemicals that find a variety of industrial uses. For example, ethylene can be used as a monomer or comonomer for producing a polyolefin. Other uses of unsaturated hydrocarbons are well known to one skilled in the art.

However, unsaturated hydrocarbons produced by a thermal cracking process generally contain an appreciable amount of less desirable highly unsaturated hydrocarbon(s) such as alkyne(s) or diolefin(s). For example, ethylene produced by thermal cracking of ethane is generally contaminated with a highly unsaturated hydrocarbon, such as acetylene, which must be selectively hydrogenated to a less unsaturated hydrocarbon, such as ethylene, but not to a saturated hydrocarbon such as ethane, in a hydrogenation process.

In addition, catalyst compositions comprising palladium and an inorganic support, such as alumina, are known catalyst compositions for the hydrogenation of highly unsaturated hydrocarbons such as alkynes and/or diolefins. For example, U.S. Pat. No. 4,484,015 discloses the use of a palladium and silver catalyst composition supported on alumina for the selective hydrogenation of acetylene to ethylene. Also for example, U.S. Pat. No. 5,510,550 discloses the use of a palladium, silver, and alkali metal catalyst composition supported on alumina for an even more selective hydrogenation of acetylene to ethylene. The operating temperature for the hydrogenation process is selected such that essentially all highly unsaturated hydrocarbon such as alkyne (e.g., acetylene) is hydrogenated to its corresponding less unsaturated hydrocarbon such as alkene (e.g., ethylene) thereby removing the alkyne from the product stream while only an insignificant amount of alkene is hydrogenated to a saturated hydrocarbon such as alkane (e.g., ethane). Such selective hydrogenation process minimizes the loss of desired less unsaturated hydrocarbons.

Thus, the development of a catalyst composition, a process of treating such catalyst composition, and a process of using such catalyst composition for the hydrogenation of highly unsaturated hydrocarbons such as diolefins (alkadienes) or alkynes to less unsaturated hydrocarbons such as monoolefins (alkenes) where such catalyst composition has improved selectivity, increased activity, and/or longer operating life would be a significant contribution to the art and to the economy.

SUMMARY OF THE INVENTION

An object of the present invention is to provide an improved process of treating a hydrogenation catalyst composition, such as a palladium-containing hydrogenation catalyst composition, and a catalyst composition prepared according to such treatment process.

Another object of the present invention is to utilize a catalyst composition treated by a process of the present invention to hydrogenate a highly unsaturated hydrocarbon, such as acetylene, in admixture with a less unsaturated hydrocarbon, such as ethylene, to produce a further amount of less unsaturated hydrocarbon, such as ethylene, without the concurrent consumption of a significant portion of such less unsaturated hydrocarbon.

According to an embodiment of the present invention, a catalyst composition is provided which can be used for selectively hydrogenating a highly unsaturated hydrocarbon such as, for example, an alkyne or a diolefin. Such catalyst composition can be prepared by a process which comprises treating a hydrogenation catalyst composition, such as a palladium-containing hydrogenation catalyst composition, by contacting such catalyst composition with a first treating agent to provide a treated catalyst composition followed by optionally contacting with a second treating agent. Generally, such first treating agent comprises carbon monoxide. Generally, such second treating agent comprises a hydrogen-containing fluid.

According to another embodiment of the present invention, a process which can be used for selectively hydrogenating a highly unsaturated hydrocarbon to a less unsaturated hydrocarbon is provided. The process comprises contacting a highly unsaturated hydrocarbon with hydrogen, in the presence of a catalyst composition which has been treated according to a process of the present invention, under a condition sufficient to effect a selective hydrogenation of the highly unsaturated hydrocarbon.

Other objects and advantages of the present invention will be apparent from the detailed description of the present invention and the appended claims.

DETAILED DESCRIPTION OF THE INVENTION

As used in the present invention, the term "fluid" denotes gas, liquid, vapor, or combinations thereof. The term "palladium" refers to palladium metal. The term "silver" refers to silver metal. The term "substantial" or "substantially" generally means more than trivial. The term "saturated hydrocarbon" refers to any hydrocarbon which does not contain any carbon-to-carbon double bonds or carbon-to-carbon triple bonds. Examples of saturated hydrocarbons include, but are not limited to, ethane, propane, butanes, pentanes, hexanes, octanes, decanes, naphtha, and the like and combinations thereof.

The term "highly unsaturated hydrocarbon" refers to a hydrocarbon having a triple bond or two or more double bonds between carbon atoms in the molecule. Examples of highly unsaturated hydrocarbons include, but are not limited to, aromatic compounds such as benzene and naphthalene; alkynes such as acetylene, propyne (also referred to as methylacetylene), and butynes; diolefins such as propadiene, butadienes, pentadienes (including isoprene), hexadienes, octadienes, and decadienes; and the like and combinations thereof.

The term "less unsaturated hydrocarbon" refers to a hydrocarbon in which a triple bond in a highly unsaturated hydrocarbon is hydrogenated to a double bond or a hydrocarbon in which the number of double bonds is one less, or at least one less, than that in the highly unsaturated hydrocarbon. Examples of less unsaturated hydrocarbons include, but are not limited to, monoolefins such as ethylene, propylene, butenes, pentenes, hexenes, octenes, decenes, and the like and combinations thereof.

The term "hydrogenation process" refers to a process which converts a highly unsaturated hydrocarbon such as an alkyne or a diolefin to a less unsaturated hydrocarbon such as a monoolefin or a saturated hydrocarbon such as an alkane. The term "selective" refers to such hydrogenation process in which a highly unsaturated hydrocarbon such as an alkyne or a diolefin is converted to a less unsaturated hydrocarbon such as a monoolefin without further hydrogenating the less unsaturated hydrocarbon to a saturated hydrocarbon such as an alkane. Thus, for example, when a highly unsaturated hydrocarbon is converted to a less unsaturated hydrocarbon without further hydrogenating such less unsaturated hydrocarbon to a saturated hydrocarbon, the hydrogenation process is "more selective" than when such highly unsaturated hydrocarbon is hydrogenated to a less unsaturated hydrocarbon and then further hydrogenated to a saturated hydrocarbon.

The term "gas hourly space velocity" refers to the numerical ratio of the rate at which a treating agent, such as a first or second treating agent of the present invention, is charged to a treating zone of the present invention (or the numerical ratio of the rate at which a hydrocarbon-containing fluid of the present invention is charged to a hydrogenation zone of the present invention) in liters per hour at standard condition of temperature and pressure ("STP") divided by the liters of catalyst composition contained in the treating zone to which the treating agent is charged (or the liters of treated catalyst composition contained in the hydrogenation zone to which the hydrocarbon-containing fluid is charged).

The term "treated catalyst composition" refers to a catalyst composition which has been subjected to a treating process of the present invention.

According to an embodiment of the present invention, a catalyst composition which can be used to selectively hydrogenate a highly unsaturated hydrocarbon (such as an alkyne or a diolefin) to a less unsaturated hydrocarbon (such as an alkene or a monoolefin) is provided. The catalyst composition comprises (a) palladium such as palladium metal, palladium oxide, or combinations thereof, (b) a catalyst component selected from the group consisting of silver, modifiers, and the like and combinations thereof, and (c) an inorganic support. The palladium can be present as "skin" on or near the surface of the catalyst composition and the catalyst component can be distributed as skin with the palladium or throughout the catalyst composition. An example of a suitable modifier includes, but is not limited to, an alkali metal compound. The catalyst composition to be treated according to a process of the present invention can be any suitable commercially available catalyst composition which, after being subjected to a treating process of the present invention, can be used to selectively hydrogenate a highly unsaturated hydrocarbon (such as an alkyne or a diolefin) to a less unsaturated hydrocarbon (such as an alkene or a monoolefin) according to a process of the present invention. The catalyst composition subjected to a treating process of the present invention can be a new catalyst composition or a regenerated catalyst composition. A treated catalyst composition of the present invention has an improved selectivity, an increased activity, and/or a longer operating life than a catalyst composition which has not been treated according to a treating process of the present invention.

A suitable commercially available catalyst composition which can be treated according to a process of the present invention can be made by any manner or method(s) known in the art. For example, the palladium and catalyst component(s) may be incorporated into, onto, or with the inorganic support by any suitable means or method(s) for incorporating the palladium and catalyst component(s) into, onto, or with a substrate material, such as an inorganic support, which results in the formation of a palladium and catalyst component-incorporated inorganic support which can then be dried and calcined to thereby provide a catalyst composition which can then be subjected to a treatment process of the present invention. Examples of means or method(s) for incorporating include, but are not limited to, impregnating, soaking, spraying, and the like and combinations thereof. A preferred method of incorporating is soaking.

The term "skin" refers to the exterior surface of the catalyst composition which can contain components, such as palladium, of the catalyst composition. The skin can be any thickness as long as such thickness can promote the hydrogenation process(es) disclosed herein. Generally, the thickness of the skin is at least about 5 microns. Generally, the thickness of the skin is no more than about 1000 microns, preferably no more than about 750 microns. Preferably, the palladium is concentrated in the skin of the catalyst composition whereas the catalyst component is distributed throughout the catalyst composition. Various skin catalyst compositions have been developed. See for example U.S. Pat. No. 4,404,124 and U.S. Pat. No. 4,484,015, the disclosures of which are incorporated herein by reference.

Generally, palladium can be present in the catalyst composition in any weight percent so long as the palladium is substantially concentrated as skin on or near the surface of the catalyst composition and that the resulting catalyst composition is effective in selectively hydrogenating a highly unsaturated hydrocarbon (such as an alkyne) to a less unsaturated hydrocarbon (such as an alkene). Generally, the catalyst composition comprises at least about 0.0001 weight percent palladium based on the total weight of the composition, preferably at least about 0.0005 weight percent palladium, and more preferably at least about 0.001 weight percent palladium. Generally, the catalyst composition comprises no more than about 3 weight percent palladium based on the total weight of the composition, preferably no more than about 1.5 weight percent palladium, and more preferably no more than about 1.0 weight percent palladium.

Examples of suitable palladium compounds which can be used for incorporating the palladium of such palladium compounds into, onto, or with an inorganic support include, but are not limited to, palladium bromide, palladium chloride, palladium iodide, palladium nitrate, palladium nitrate hydrate, tetraamine palladium nitrate, palladium oxide, palladium oxide hydrate, palladium sulfate, and the like and combinations thereof. The palladium can have any available oxidation state. The presently preferred palladium compound is $H_2PdCl_4$. When added to the support by impregnation from solution, some of the compounds can be added from aqueous solution, but others will require non-aqueous solvents such as alcohols, hydrocarbons, ethers, ketones and the like.

When the catalyst composition comprises a catalyst component comprising silver, the silver can be present in the catalyst composition in any weight percent as long as the resulting catalyst composition is effective in selectively hydrogenating a highly unsaturated hydrocarbon (such as an alkyne) to a less unsaturated hydrocarbon (such as an alkene). Generally, the catalyst composition comprises at least about 0.0003 weight percent silver based on the total weight of the composition, preferably at least about 0.003 weight percent silver based on the total weight of the catalyst composition, and more preferably at least about 0.005 weight percent silver. Generally, the catalyst composition comprises no more than about 20 weight percent silver based on the total weight of the composition, preferably no more than about 10 weight percent silver, and more preferably no more than about 5 weight percent silver.

Suitable examples of silver compounds for use in incorporating, preferably impregnating, the silver of such silver compound(s) into, onto, or with an inorganic support include, but are not limited to, silver nitrate, silver acetate, silver cyanide and the like and combinations thereof. The presently preferred silver compound is silver nitrate.

In lieu of a catalyst component comprising silver or in addition to a catalyst component comprising silver, the catalyst composition can comprise a catalyst component comprising a modifier, preferably an alkali metal compound. Any alkali metal compound(s) can be used in preparing a catalyst composition of the present invention as long as the resulting catalyst composition is effective in selectively hydrogenating a highly unsaturated hydrocarbon (such as an alkyne) to a less unsaturated hydrocarbon (such as an alkene). Suitable examples of alkali metal compounds for use in incorporating, preferably impregnating, the alkali metal compound(s) into, onto, or with the inorganic support generally include, but are not limited to, alkali metal halides, alkali metal hydroxides, alkali metal carbonates, alkali metal bicarbonates, alkali metal nitrates, alkali metal carboxylates, and the like and combinations thereof. Preferably, the alkali metal compound is an alkali metal halide, more preferably the alkali metal compound is an alkali metal iodide or an alkali metal fluoride. Generally, the alkali metal of such alkali metal compound is selected from the group consisting of potassium, rubidium, cesium, and the like and combinations thereof. Preferably, the alkali metal of such alkali metal compound is potassium. Preferably, the alkali metal compound is potassium iodide (KI) and, more preferably, the alkali metal compound is potassium fluoride (KF).

Further examples of suitable alkali metal compounds include, but are not limited to, sodium fluoride, lithium fluoride, rubidium fluoride, cesium fluoride, sodium iodide, lithium iodide, rubidium iodide, cesium iodide, sodium chloride, potassium chloride, lithium chloride, rubidium chloride, cesium chloride, sodium bromide, potassium bromide, lithium bromide, rubidium bromide, cesium bromide, sodium hydroxide, potassium hydroxide, lithium hydroxide, rubidium hydroxide, cesium hydroxide, sodium oxide, potassium oxide, lithium oxide, rubidium oxide, cesium oxide, sodium carbonate, potassium carbonate, lithium carbonate, rubidium carbonate, cesium carbonate, sodium nitrate, potassium nitrate, lithium nitrate, rubidium nitrate, cesium nitrate, and the like and combinations thereof.

Generally, the catalyst composition comprises a modifier, preferably an alkali metal. Generally, the catalyst composition comprises at least about 0.001 weight percent alkali metal based on the total weight of the catalyst composition, preferably at least about 0.005 weight percent alkali metal, and more preferably at least about 0.01 weight percent alkali metal. Generally, the catalyst composition comprises no more than about 10 weight percent alkali metal based on the total weight of the composition, preferably no more than about 5 weight percent alkali metal, and more preferably no more than about 2 weight percent alkali metal. Generally, the weight ratio of alkali metal to palladium is at least about 0.05:1, preferably at least about 0.1:1, and more preferably at least about 0.2:1. Generally, the weight ratio of alkali metal to palladium is no more than about 500:1, preferably no more than about 200:1, and more preferably no more than about 100:1.

When the catalyst composition comprises an alkali metal compound comprising an alkali metal iodide, the catalyst composition generally comprises at least about 0.03 weight percent iodine (chemically bound as iodide) (on a total catalyst composition weight basis), preferably at least about 0.1 weight percent iodine, and more preferably at least about 0.2 weight percent iodine. Generally, the catalyst composition comprises no more than about 10 weight percent iodine, preferably no more than about 5 weight percent iodine, and more preferably no more than about 1 weight percent iodine. Generally, the atomic ratio of iodine to alkali metal is at least about 0.5:1, and preferably at least about 1:1. Generally, the atomic ratio of iodine to alkali metal is no more than about 4:1, and preferably no more than about 3:1. When the alkali metal compound is an alkali metal iodide, it should be used in lieu of silver.

When the catalyst composition comprises an alkali metal compound comprising an alkali metal fluoride, the catalyst composition generally comprises at least about 0.02 weight percent fluorine (chemically bound as fluoride) (on a total catalyst composition weight basis), preferably at least about 0.1 weight percent fluorine, and more preferably at least about 0.2 weight percent fluorine. Generally, the catalyst composition comprises no more than about 10 weight percent fluorine, preferably no more than about 5 weight percent fluorine, and more preferably no more than about 1 weight percent fluorine. Generally, the atomic ratio of fluorine to alkali metal is at least about 0.5:1, and preferably at least about 1:1. Generally, the atomic ratio of fluorine to alkali metal is no more than about 4:1, and preferably no more than about 3:1.

The inorganic support can be any inorganic solid support material suitable for use in a hydrogenation catalyst composition of the present invention. Preferably, the inorganic support is selected from the group consisting of alumina, aluminates, titania, zirconia, and the like and combinations thereof. The presently more preferred support material is alumina, most preferably alpha-alumina.

The catalyst composition can have any suitable shape or form as long as such shape or form is effective in selectively hydrogenating a highly unsaturated hydrocarbon (such as an alkyne) to a less unsaturated hydrocarbon (such as an alkene) according to a process of the present invention. Suitable examples of forms which a catalyst composition of the present invention include, but are not limited to, tablets, pellets, extrudates, spheres, and the like and combinations thereof. A catalyst composition of the present invention generally has a particle size of at least about 0.5 millimeters (mm), and preferably at least about 1 mm. Generally, a catalyst composition has a particle size of no more than about 10 mm, preferably no more than about 8 mm, and more preferably no more than about 6 mm.

According to an embodiment of the present invention, a hydrogenation catalyst composition, preferably a palladium-containing hydrogenation catalyst composition, is subjected to a treating process of the present invention to obtain a treated catalyst composition of the present invention, preferably a treated palladium-containing hydrogenation catalyst composition. Such treated catalyst composition can then be utilized in a process of the present invention for selectively hydrogenating a highly unsaturated hydrocarbon (such as an alkyne) to a less unsaturated hydrocarbon (such as an alkene) where such treated catalyst composition has an improved selectivity, an increased activity, and/or a longer operating life than a catalyst composition which has not been treated according to a treating process of the present invention.

A treating process of the present invention comprises contacting a catalyst composition, preferably a palladium-containing catalyst composition, with a first treating agent comprising carbon monoxide under a first treating condition effective to provide a treated catalyst composition.

The first treating agent comprises carbon monoxide. In addition to carbon monoxide, the first treating agent can further comprise an additional component. Examples of such additional component of a first treating agent of the present invention include, but are not limited to, a hydrogen-containing fluid such as hydrogen gas, an inert gas, a hydrocarbon-containing gas, and the like and combinations thereof. Examples of a suitable inert gas include, but are not limited to, nitrogen, argon, and the like and combinations thereof. Examples of a suitable hydrocarbon-containing gas include, but are not limited to, methane and the like and combinations thereof. The hydrocarbon-containing gas can be obtained from any suitable, available source such as the tail gas from a refinery.

An example of a first treating agent of the present invention comprises carbon monoxide in the form of formic acid vapor diluted in an inert gas, preferably nitrogen. A preferred first treating agent of the present invention comprises carbon monoxide as a dilute stream with an inert gas, preferably nitrogen, as the diluent. Another preferred first treating agent of the present invention is a hydrogen-containing fluid which contains carbon monoxide. Preferably, such hydrogen-containing fluid is hydrogen gas.

A first treating agent of the present invention comprises a mole percentage of carbon monoxide (CO) of generally at least about 0.0005, preferably at least about 0.005, and more preferably at least about 0.01. A first treating agent of the present invention comprises a mole percentage of CO of generally no more than about 50, preferably no more than about 25, and more preferably no more than about 10.

Treating a catalyst composition with a first treating agent according to a process of the present invention is generally carried out by contacting such catalyst composition with a first treating agent under a first treating condition as disclosed herein. The catalyst composition, which can be contained within a treating zone, can be contacted by any suitable manner with a first treating agent under a first treating condition as described herein. Such treating zone can comprise, for example, a reactor vessel.

A first treating condition of the present invention comprises a temperature of at least about 50° F., preferably at least about 100° F., and more preferably at least about 200° F. Generally, the first treating condition comprises a temperature of no more than about 800° F., preferably no more than about 600° F., and more preferably no more than about 500° F. The first treating condition also comprises a pressure of at least about atmospheric (i.e., about 14.7 pounds per square inch absolute) and generally no more than about 150 pounds per square inch absolute (psia), preferably no more than about 100 (psia). The pressure is more preferably about atmospheric. The first treating condition also comprises a time period generally of at least about 0.1 hour and generally no more than about 50 hours, preferably no more than about 40 hours, and more preferably no more than about 30 hours.

A first treating condition of the present invention further comprises the flow rate at which the first treating agent comprising carbon monoxide is charged (i.e., the charge rate of first treating agent) to the treating zone. The flow rate is such as to provide a gas hourly space velocity ("GHSV") generally exceeding 1 liter of first treating agent per liter of catalyst composition per hour (liter/liter/hour). The term "gas hourly space velocity" has been described herein. Generally, the gas hourly space velocity of the first treating agent will be at least about 1 liter/liter/hour, preferably at least about 500 liter/liter/hour, and more preferably at least about 750 liter/liter/hour. Generally, the gas hourly space velocity of the first treating agent will be no more than about 50,000 liter/liter/hour, preferably no more than about 40,000 liter/liter/hour, and more preferably no more than about 30,000 liter/liter/hour.

Treating a catalyst composition with a first treating agent under a first treating condition according to a process of the present invention can be operated as a batch process or, preferably, as a continuous process. In the latter operation, a solid or fixed catalyst bed or a moving catalyst bed or a fluidized catalyst bed can be employed. Preferably, a fixed catalyst bed is employed. Any of these operational modes have advantages and disadvantages, and those skilled in the art can select the one most suitable for a particular catalyst composition and first treating agent.

Optionally, after contacting a catalyst composition with a first treating agent under a first treating condition as disclosed herein, the thus-treated catalyst composition can be further contacted with a second treating agent under a second treating condition as disclosed herein.

The second treating agent comprises a hydrogen-containing fluid. In addition to a hydrogen-containing fluid, the second treating agent can further comprise an additional component. Examples of such additional component of a second treating agent of the present invention include, but are not limited to, carbon monoxide, an inert gas, a hydrocarbon-containing gas, and the like and combinations thereof. Examples of a suitable inert gas include, but are not limited to, nitrogen, argon, and the like and combinations thereof. Examples of a suitable hydrocarbon-containing gas include, but are not limited to, methane and the like and combinations thereof. The hydrocarbon-containing gas can be obtained from any suitable, available source such as the tail gas from a refinery.

A second treating agent of the present invention is preferably a hydrogen-containing fluid. More preferably, a second treating agent of the present invention is hydrogen gas. Most preferably, a second treating agent of the present invention is hydrogen gas having a purity of greater than about 98%.

A second treating agent of the present invention comprises a mole percentage of carbon monoxide (CO) of generally at least about 0.0005, preferably at least about 0.005, and more preferably at least about 0.01. A second treating agent of the present invention comprises a mole percentage of CO of generally no more than about 50, preferably no more than about 25, and more preferably no more than about 10.

Further treating a treated catalyst composition of the present invention (i.e., a catalyst composition which has been contacted with a first treating agent as disclosed herein) with a second treating agent according to a process of the present invention is generally carried out by contacting such treated catalyst composition with a second treating agent under a second treating condition as disclosed herein. The treated catalyst composition, which can be contained within a treating zone, can be contacted by any suitable manner with a second treating agent under a second treating condition as disclosed herein. Such treating zone can comprise, for example, a reactor vessel.

A second treating condition of the present invention comprises a temperature of at least about 50° F., preferably at least about 100° F., and more preferably at least about 200° F. Generally, the second treating condition comprises a temperature of no more than about 800° F., preferably no more than about 600° F., and more preferably no more than about 500° F. The second treating condition also comprises a pressure of at least about atmospheric (i.e., about 14.7 pounds per square inch absolute), and generally no more than about 150 pounds per square inch absolute (psia), preferably no more than about 100 psia. The pressure is more preferably about atmospheric. The second treating condition also comprises a time period generally of at least about 0.1 hour and generally no more than about 50 hours, preferably no more than about 40 hours, and more preferably no more than about 30 hours.

A second treating condition of the present invention further comprises the flow rate at which the second treating agent, preferably a hydrogen-containing fluid, is charged (i.e., the charge rate of second treating agent) to the treating zone. The flow rate is such as to provide a gas hourly space velocity ("GHSV") generally exceeding 1 liter of second treating agent per liter of catalyst composition per hour (liter/liter/hour). The term "gas hourly space velocity" has been described herein. Generally, the gas hourly space velocity of the second treating agent will be at least about 1 liter/liter/hour, preferably at least about 500 liter/liter/hour, and more preferably at least about 750 liter/liter/hour. Generally, the gas hourly space velocity of the second treating agent will be no more than about 50,000 liter/liter/hour, preferably no more than about 40,000 liter/liter/hour, and more preferably no more than about 30,000 liter/liter/hour.

Further treating a treated catalyst composition of the present invention with a second treating agent under a second treating condition according to a process of the present invention can be operated as a batch process or, preferably, as a continuous process. In the latter operation, a solid or fixed catalyst bed or a moving catalyst bed or a fluidized catalyst bed can be employed. Preferably, a fixed catalyst bed is employed. Any of these operational modes have advantages and disadvantages, and those skilled in the art can select the one most suitable for a particular catalyst composition and second treating agent.

In a more preferred treating process of the present invention, a catalyst composition is contacted with a first treating agent (preferably a hydrogen-containing fluid which contains carbon monoxide, more preferably a hydrogen gas stream which contains carbon monoxide) under a first treating condition to provide a treated catalyst composition. The carbon monoxide being provided to such hydrogen-containing fluid is then stopped allowing a hydrogen-containing fluid (preferably hydrogen gas) to continue contacting the treated catalyst composition under a second treating condition to further treat the treated catalyst composition.

According to another embodiment of the present invention, a hydrogenation process is provided. The hydrogenation process of this invention can comprise contacting a hydrocarbon-containing fluid which comprises one or more highly unsaturated hydrocarbon(s) such as an aromatic hydrocarbon(s), alkyne(s), and/or diolefin(s) with a treated catalyst composition of the present invention in the presence of hydrogen in a hydrogenation zone under a hydrogenation condition to hydrogenate such one or more highly unsaturated hydrocarbon(s) to a less unsaturated hydrocarbon such as a monoolefin. The highly unsaturated hydrocarbon(s) is present in the hydrocarbon-containing fluid as an impurity generally at a level found in typical commercial feed streams. Generally, the hydrocarbon-containing fluid comprises at least about 1 part by weight highly unsaturated hydrocarbon(s) per billion parts by weight hydrocarbon-containing fluid (i.e., about 1 ppb), typically at least about 10 ppb, and more typically at least about 100 ppb. Generally, the hydrocarbon-containing fluid comprises no more than about 10 weight percent highly unsaturated hydrocarbon, typically no more than about 8 weight percent, and more typically no more than about 3 weight percent.

Hydrogen can be present either in the hydrocarbon-containing fluid or in a hydrogen-containing fluid which is mixed with the hydrocarbon-containing fluid before contacting with a treated catalyst composition of the present invention. If a hydrogen-containing fluid is used, it can be a hydrogen gas stream or any fluid containing a sufficient concentration of hydrogen to effect the hydrogenation disclosed herein. It can also contain other gases such as, for example, nitrogen, methane, carbon monoxide, carbon dioxide, steam, or combinations thereof so long as the hydrogen-containing fluid contains a sufficient concentration of hydrogen to effect the hydrogenation disclosed herein.

The hydrocarbon-containing fluid of the hydrogenation process(es) of the present invention can also comprise one or more less unsaturated hydrocarbon(s) such as a monoolefin(s) and one or more saturated hydrocarbon(s) such as an alkane(s). These additional hydrocarbons can be present in the hydrocarbon-containing fluid at a level of at least about 0.001 weight percent and no more than about 99.999 weight percent.

Examples of suitable alkynes include, but are not limited to, acetylene, propyne (also referred to as methylacetylene), 1-butyne, 2-butyne, 1-pentyne, 2-pentyne, 3-methyl-1-butyne, 1-hexyne, 1-heptyne, 1-octyne, 1-nonyne, 1-decyne, and the like and combinations thereof. The presently preferred alkynes are acetylene and propyne.

The alkynes are primarily hydrogenated to the corresponding alkenes. For example, acetylene is primarily hydrogenated to ethylene; propyne is primarily hydrogenated to propylene; and the butynes are primarily hydrogenated to the corresponding butenes (e.g., 1-butene, 2-butenes).

Examples of suitable diolefins include those generally containing at least about 3 carbon atoms per molecule and generally containing no more than about 12 carbon atoms per molecule. Such diolefins include, but are not limited to, propadiene, 1,2-butadiene, 1,3-butadiene, isoprene, 1,2-pentadiene, 1,3-pentadiene, 1,4-pentadiene, 1,2-hexadiene, 1,3-hexadiene, 1,4-hexadiene, 1,5-hexadiene, 2-methyl-1,2-pentadiene, 2,3-dimethyl-1,3-butadiene, heptadienes, methylhexadienes, octadienes, methylheptadienes, dimethylhexadienes, ethylhexadienes, trimethylpentadienes, methyloctadienes, dimethylheptadienes, ethyloctadienes, trimethylhexadienes, nonadienes, decadienes, undecadienes, dodecadienes, cyclopentadienes, cyclohexadienes, methylcyclopentadienes, cycloheptadienes, methylcyclohexadienes, dimethylcyclopentadienes, ethylcyclopentadienes, dicyclopentadiene (also known as tricyclo$[5.2.1]^{2,6}$deca-3,8-diene), and the like and combinations thereof.

Presently preferred diolefins are propadiene, 1,2-butadiene, 1,3-butadiene, pentadienes (such as 1,3-pentadiene, 1,4-pentadiene, isoprene), cyclopentadienes (such as 1,3-cyclopentadiene) and dicyclopentadiene. These diolefins are preferably hydrogenated to their corresponding monoolefins containing the same number of carbon atoms per molecule as the diolefins. For example, propadiene is hydrogenated to propylene, 1,2-butadiene and 1,3-butadiene are hydrogenated to 1-butene and 2-butene, 1,3-pentadiene and 1,4-pentadiene are hydrogenated to 1-pentene and 2-pentene, isoprene is hydrogenated to methyl-1-pentenes and methyl-2-pentenes, and 1,3-cyclopentadiene is hydrogenated to cyclopentene.

Examples of suitable aromatic hydrocarbons include, but are not limited to, benzene, toluene, ethylbenzene, styrene, xylenes, and the like and combinations thereof.

Examples of suitable monoolefins include, but are not limited to, ethylene, propylene, 1-butene, 2-butene, isobutylene, 1-pentene, 2-pentene, methyl-1-butenes (such as 2-methyl-1-butene), methyl-2-butenes (such as 2-methyl-2-butene), 1-hexene, 2-hexene, 3-hexene, methyl-1-pentenes, 2,3-dimethyl-1-butene, 1-heptene, 2-heptene, 3-heptene, methyl-1-hexenes, methyl-2-hexenes, methyl-3-hexenes, dimethylpentenes, ethylpentenes, octenes, methylheptenes, dimethylhexenes, ethylhexenes, nonenes, methyloctenes, dimethylheptenes, ethylheptenes, trimethylhexenes, cyclopentene, cyclohexene, methylcyclopentene, cycloheptene, methylcyclohexene, dimethylcyclopentenes, ethylcyclopentenes, cyclooctenes, methylcycloheptenes, dimethylcyclohexenes, ethylcyclohexenes, trimethylcyclohexenes, methylcyclooctenes, dimethylcyclooctenes, ethylcyclooctenes, and the like and combinations thereof.

Examples of suitable saturated hydrocarbons include, but are not limited to, methane, ethane, propane, butane, methylpropane, methylbutane, dimethylbutane, pentanes, hexanes, and the like and combinations thereof.

Further, the hydrocarbon-containing fluid can contain up to about 5000 parts per million by volume (ppmv) of carbon monoxide.

The hydrocarbon-containing fluid disclosed herein may contain an impurity. The term "impurity" as used herein denotes any component in a hydrocarbon-containing fluid that is not a major component. Examples of impurities other than an alkyne or a diolefin include, but are not limited to, carbon monoxide, hydrogen sulfide, carbonyl sulfide (COS), carbon disulfide ($CS_2$), mercaptans (RSH), organic sulfides (RSR), organic disulfides (RSSR), thiophene, organic trisulfides, organic tetrasulfides, and the like and combinations thereof, wherein each R can be an alkyl or cycloalkyl or aryl group containing at least about 1 carbon atom and generally no more than about 15 carbon atoms, preferably no more than about 10 carbon atoms. It is within the scope of this invention to have additional compounds (such as water, alcohols, ethers, aldehydes, ketones, carboxylic acids, esters, other oxygenated compounds, and the like and combinations thereof) present in the hydrocarbon-containing fluid, as long as they do not significantly interfere with the hydrogenation process of a highly unsaturated hydrocarbon to a less unsaturated hydrocarbon as described herein.

The hydrogenation process(es) of the present invention is generally carried out by contacting a hydrocarbon-containing fluid comprising at least one highly unsaturated hydrocarbon, in the presence of hydrogen, with a treated catalyst composition of the present invention under a hydrogenation condition. The hydrocarbon-containing fluid can be contacted by any suitable manner with the treated catalyst composition which is contained within a hydrogenation zone. Such hydrogenation zone can comprise, for example, a reactor vessel. The treating zone and hydrogenation zone of the present invention can be the same zone or different zones. For example, a treating process of the present invention can be conducted in a treating zone comprising a reactor vessel. After completing the treatment process described herein, a hydrogenation process of the present invention can then be conducted in the same reactor vessel.

The contacting step, of contacting a hydrocarbon-containing fluid with a treated catalyst composition of the present invention, can be operated as a batch process step or, preferably, as a continuous process step. In the latter operation, a solid or fixed catalyst bed or a moving catalyst bed or a fluidized catalyst bed can be employed. Preferably, a fixed catalyst bed is employed. Any of these operational modes have advantages and disadvantages, and those skilled in the art can select the one most suitable for a particular hydrocarbon-containing fluid and treated catalyst composition.

The contacting step is preferably carried out within a hydrogenation zone, wherein is contained a treated catalyst composition of the present invention, and under a hydrogenation condition that suitably promotes the hydrogenation process of a highly unsaturated hydrocarbon to a less unsaturated hydrocarbon. Such hydrogenation condition should be such as to avoid significant hydrogenation of a less unsaturated hydrocarbon(s) being initially present in the hydrocarbon-containing fluid to a saturated hydrocarbon(s) such as an alkane(s) or cycloalkane(s).

Generally, such hydrogenation process comprises the presence of hydrogen, preferably hydrogen gas, in an amount of at least about 0.1 mole of hydrogen employed for each mole of highly unsaturated hydrocarbon present in the hydrocarbon-containing fluid, preferably at least about 0.5 mole of hydrogen, and more preferably at least about 0.7 mole of hydrogen. Generally, such hydrogenation process comprises no more than about 1000 moles of hydrogen employed for each mole of highly unsaturated hydrocarbon present in the hydrocarbon-containing fluid, preferably no more than about 500 moles of hydrogen, and more preferably no more than about 200 moles of hydrogen.

Generally, such hydrogenation condition comprises a temperature and a pressure necessary for the hydrogenation process(es) of the present invention depending largely upon the activity of the treated catalyst composition, the hydrocarbon-containing fluid, and the desired extent of hydrogenation. Generally, such temperature is at least about 50° F., preferably at least about 60° F., and more preferably at least about 70° F. Generally, such temperature is no more than about 600° F., preferably no more than about 500° F., and more preferably no more than about 400° F. A suitable pressure is generally at least about 15 pounds per square inch gauge (psig), preferably at least about 50 psig, and more preferably at least about 100 psig. Generally, a suitable pressure is no more than about 2000 psig, preferably no more than about 1500 psig, and more preferably no more than about 1000 psig.

Such hydrogenation condition further comprises the flow rate at which the hydrocarbon-containing fluid is charged (i.e., the charge rate of hydrocarbon-containing fluid) to the hydrogenation zone. The flow rate is such as to provide a gas hourly space velocity ("GHSV") generally exceeding 1 liter of hydrocarbon-containing fluid per liter of treated catalyst composition per hour (liter/liter/hour). The term "gas hourly space velocity" has been described herein. Typically, the gas hourly space velocity of the hydrocarbon-containing fluid will be at least about 1 liter/liter/hour, preferably at least about 750 liter/liter/hour, and more preferably at least about 1000 liter/liter/hour. Typically, the gas hourly space velocity will be no more than about 50,000 liter/liter/hour, preferably no more than about 40,000 liter/liter/hour, and more preferably no more than about 30,000 liter/liter/hour.

If it is desired to regenerate a treated catalyst composition of the present invention after prolonged use in a hydrogenation process(es) described herein, the regeneration can be accomplished by calcining the treated catalyst composition in an oxidizing atmosphere such as in air at a temperature that does not exceed about 1300° F. to burn off carbonaceous and sulfur deposits. Optionally, the catalyst composition can be reimpregnated with palladium and a catalyst component comprising either silver or an alkali metal compound, or both silver and an alkali metal compound, and then dried and calcined for the production of a fresh catalyst composition which can then be subjected to a treating process of the present invention to provide a treated catalyst composition.

The following examples are presented to further illustrate the present invention and are not to be construed as unduly limiting the scope of the present invention.

EXAMPLES

Example I

This example describes the untreated catalyst composition, catalyst composition treating process, and reaction process utilized in Examples II through V unless otherwise noted in such Examples.

Catalyst A was a commercially-available material designated "G58D" obtained from United Catalysts Inc., Louisville, Ky. Catalyst A contained 0.016 to 0.018 weight percent palladium and 0.11 weight percent silver on aluminum oxide support.

The catalyst treating process was conducted as follows. About 20 cc (23 grams) of the above-described Catalyst A were mixed with 40 mL of alundum (an inert material) and placed in a stainless steel jacketed reactor tube having a 0.75 inch inner diameter and a length of about 18 inches. The catalyst resided in the middle of the reactor and both ends of the reactor were packed with about 10 cc of alundum. The reaction temperature was controlled by circulating ethylene glycol through the jacket of the reactor tube. The catalyst was then treated by contacting the catalyst with a first treating agent by passing such first treating agent over the catalyst at 200 milliliters per minute (mL/min) at atmospheric pressure at 395° F. for two hours to provide a treated catalyst. In some of the Examples, the treated catalyst was then contacted with a second treating agent by passing such second treating agent over the treated catalyst at 200 mL/min at atmospheric pressure at 395° F. for two hours.

The reaction process was then conducted as follows. A feed gas (approximately: 15 wt % methane, 83 wt % ethylene, 1.1 wt % acetylene, and 0.1 wt % hydrogen (1.3 hydrogen to acetylene molar ratio)) was contacted with the catalyst by passing the feed gas over the catalyst at about 913 cc/min at 200 pounds per square inch gauge (psig). The reaction temperature was varied to yield a specific conversion of acetylene. Conversion of acetylene is defined as the percent of acetylene that was consumed from the feed gas. The temperature was then held constant for 24 to 48 hours with the feed continually contacting, i.e., passing over, the catalyst. Samples of the product were analyzed at various time intervals by means of a gas chromatograph. After about 20 to 40 hours, the reactor temperature was varied to achieve a conversion of acetylene between 80% and 100%. Selectivities were calculated on a weight basis from the gas chromatography data.

Example II

This example demonstrates the effect of using carbon monoxide as the first treating agent. All runs utilized Catalyst A, the catalyst treating process, and the reaction process as described herein in Example I, except a second treating agent was not used. Control Run 2A utilized hydrogen gas as the first treating agent. Invention Run 2B utilized 5 mole percent carbon monoxide in hydrogen gas as the first treating agent. Invention Run 2C utilized 5 mole percent carbon monoxide in nitrogen gas as the first treating agent. The results of Example II are shown in Table I.

TABLE I

| RUN | TYPE | FIRST ACTIVATING AGENT | 80% CONVERSION | | 90% CONVERSION | | MAXIMUM CONVERSION | | |
|---|---|---|---|---|---|---|---|---|---|
| | | | TEMP. (° F.) | SELECTIVITY TO ETHYLENE | TEMP. (° F.) | SELECTIVITY TO ETHYLENE | CONVERSION | TEMP. (° F.) | SELECTIVITY TO ETHYLENE |
| 2A | Control | $H_2$ | 117 | 64 | 123 | 60 | 99.6 | 146 | 16 |
| 2B | Invention | 5% $CO/H_2$ | 99 | 59 | 105 | 55 | 99.4 | 120 | 20 |
| 2C | Invention | 5% $CO/N_2$ | 89 | 58 | 97 | 43 | 98.4 | 150 | 29 |

The data in Table I clearly demonstrate that a first treating agent comprising carbon monoxide significantly lowered the reaction temperature for a given conversion.

Example III

This example demonstrates the effect of utilizing a first treating agent comprising carbon monoxide followed by utilizing a second treating agent comprising hydrogen gas. All runs utilized Catalyst A, the catalyst treating process, and the reaction process as described herein in Example I. Control Run 3A utilized hydrogen gas as the first treating agent without utilizing a second treating agent. Control Run 3B utilized hydrogen gas as both the first and second treating agent. Invention Run 3C utilized 5 mole percent carbon monoxide in hydrogen gas as the first treating agent and hydrogen gas as the second treating agent. Invention Run 3D utilized 5 mole percent carbon monoxide in nitrogen gas as the first treating agent and hydrogen gas as the second treating agent. The results of Example III are shown in Table II.

TABLE II

| | | | | 80% CONVERSION | | 90% CONVERSION | | MAXIMUM CONVERSION | | |
|---|---|---|---|---|---|---|---|---|---|---|
| RUN | TYPE | FIRST ACTIVATING AGENT | SECOND ACTIVATING AGENT | TEMP. (° F.) | SELECTIVITY TO ETHYLENE | TEMP. (° F.) | SELECTIVITY TO ETHYLENE | CONVERSION | TEMP. (° F.) | SELECTIVITY TO ETHYLENE |
| 3A | Control | $H_2$ | — | 117 | 64 | 123 | 60 | 99.6 | 146 | 16 |
| 3B | Control | $H_2$ | $H_2$ | 134 | 64 | 139 | 54 | 99.5 | 195 | −4 |
| 3C | Invention | 5% CO/$H_2$ | $H_2$ | 101 | 66 | 108 | 61 | 99.2 | 156 | 18 |
| 3D | Invention | 5% CO/$N_2$ | $H_2$ | — | — | 107 | 56 | 99.6 | 172 | 15 |

The data in Table II clearly demonstrate that the catalyst is less active (the reaction temperature increases) and selectivity at higher conversions is less when the catalyst is contacted for a longer period of time with a treating agent of hydrogen gas (compare Runs 3A and 3B). The data in Table II also clearly demonstrate that utilizing a first treating agent of 5 mole percent carbon monoxide in hydrogen gas followed by contacting with a second treating agent of hydrogen gas (Invention Run 3C) provides a more active catalyst (lower reaction temperature) at lower conversions with relatively similar selectivity at all conversions (compare Invention Run 3C to Control Runs 3A and 3B). The data in Table II also clearly demonstrate that utilizing a first treating agent of 5 mole percent carbon monoxide in nitrogen gas followed by contacting with a second treating agent of hydrogen gas (Invention Run 3D) provides a significantly more active (lower reaction temperature) and selective catalyst at 90% conversion (compare Invention Run 3D to Control Runs 3A and 3B).

manner as Control Run 4C except that contacting with a second treating agent was not conducted. Invention Run 4E utilized 5 mole percent carbon monoxide in nitrogen gas as the first treating agent ex situ (i.e., contacting with the first treating agent was conducted outside the stainless steel jacketed reactor tube in a separate glass-tube reactor under the conditions as described herein in Example I) followed by cooling to room temperature, exposing to air, loading the catalyst into the stainless steel jacketed reactor tube followed by contacting with a second treating agent of hydrogen gas in situ. Invention Run 4F was conducted in the same manner as Invention Run 4E with the exception that, once the catalyst was loaded into the stainless steel jacketed reactor tube, the reactor was pressurized and depressurized three times with hydrogen gas to 200 pounds per square inch gauge (psig) to help remove any traces of air instead of contacting with a second treating agent. The results of Example IV are shown in Table III.

TABLE III

| | | | | 80% CONVERSION | | 90% CONVERSION | | MAXIMUM CONVERSION | | |
|---|---|---|---|---|---|---|---|---|---|---|
| RUN | TYPE | FIRST ACTIVATING AGENT | SECOND ACTIVATING AGENT | TEMP. (° F.) | SELECTIVITY TO ETHYLENE | TEMP. (° F.) | SELECTIVITY TO ETHYLENE | CONVERSION | TEMP. (° F.) | SELECTIVITY TO ETHYLENE |
| 4A | Control | $H_2$* | — | 117 | 64 | 123 | 60 | 99.6 | 146 | 16 |
| 4B | Control | $H_2$* | $H_2$* | 134 | 64 | 139 | 54 | 99.5 | 195 | −4 |
| 4C | Invention | 5% CO/$N_2$* | $H_2$* | — | — | 107 | 56 | 99.6 | 172 | 15 |
| 4D | Invention | 5% CO/$N_2$* | — | 89 | 58 | 97 | 43 | 98.4 | 150 | 29 |
| 4E | Invention | 5% CO/$N_2$** | $H_2$* | 118 | 62 | — | — | 99.7 | 146 | 27 |
| 4F | Invention | 5% CO/$N_2$** | — | 116 | 66 | 122 | 52 | — | — | — |

*In situ
**Ex situ

Example IV

This example demonstrates the effect of using a first treating agent comprising carbon monoxide, both in situ and ex situ, and optionally using a second treating agent of hydrogen gas in situ. All runs utilized Catalyst A, the catalyst treating process, and the reaction process as described herein in Example I with the exceptions regarding in situ and ex situ. Control Run 4A utilized hydrogen gas, in situ, as the first treating agent without utilizing a second treating agent. Control Run 4B utilized hydrogen gas, in situ, as both the first and second treating agent. Control Run 4C utilized 5 mole percent carbon monoxide in nitrogen gas as the first treating agent followed by contacting with a second treating agent of hydrogen gas, all in situ (i.e., the catalyst was never exposed to air between contacting with the first and second treating agents). Control Run 4D was conducted in the same The data in Table III clearly demonstrate that utilizing 5 mole percent carbon monxide in nitrogen, either in situ or ex situ, yields a more active catalyst at lower conversions and a more selective catalyst at higher conversions compared to the control (compare Invention Runs 4D and 4F to Control Run 4A). The data in Table III also demonstrate that utilizing 5 mole percent carbon monoxide in nitrogen, either in situ or ex situ, followed by a second hydrogen treatment yields a catalyst that is more active than the control as well as more selective at higher conversions than the control (compare Invention Runs 4C and 4E to Control Run 4B).

Example V

This example demonstrates the effect of the carbon monoxide concentration in the first treating agent comprising such carbon monoxide and hydrogen gas. A second treating agent was not utilized. All runs utilized Catalyst A, the catalyst treating process, and the reaction process as described herein in Example I. The results of Example V are shown in Table IV.

TABLE IV

| RUN | TYPE | % CO in H₂ OF FIRST AC-TIVATING AGENT | 80% CONVERSION | | 90% CONVERSION | | MAXIMUM CONVERSION | | |
|---|---|---|---|---|---|---|---|---|---|
| | | | TEMP. (° F.) | SELECTIVITY TO ETHYLENE | TEMP. (° F.) | SELECTIVITY TO ETHYLENE | CONVERSION | TEMP. (° F.) | SELECTIVITY TO ETHYLENE |
| 5A | Control | 0 | 117 | 64 | 123 | 60 | 99.6 | 146 | 16 |
| 5B | Invention | 0.05 | 70 | 67 | 74 | 50 | 99.4 | 87 | −7 |
| 5C | Invention | 0.1 | 70 | 67 | 74 | 56 | 99.5 | 85 | 3 |
| 5D | Invention | 0.5 | 75 | 68 | 79 | 60 | 99.6 | 93 | 9 |
| 5E | Invention | 5 | 99 | 59 | 105 | 55 | 99.4 | 120 | 20 |

The data in Table IV clearly demonstrate that adding carbon monoxide in the first treating agent comprising such carbon monoxide and hydrogen gas significantly increases the catalyst's activity. The data in Table IV demonstrate that the catalyst activity is inversely proportional to the concentration of carbon monoxide in the first treating agent comprising such carbon monoxide and hydrogen gas. The data in Table IV also demonstrate that no significant change in selectivity was observed at the 80% and 90% conversions. However, at high conversion the selectivity decreased when the concentration of carbon monoxide was below approximately 0.5%.

The results shown in the above examples clearly demonstrate that the present invention is well adapted to carry out the objects and attain the ends and advantages mentioned as well as those inherent therein.

Reasonable variations, modifications, and adaptations can be made within the scope of the disclosure and the appended claims without departing from the scope of this invention.

What is claimed is:

1. A process comprising contacting a hydrocarbon-containing fluid which comprises a highly unsaturated hydrocarbon with a treated catalyst composition in the presence of hydrogen in a hydrogenation zone under a hydrogenation condition effective to hydrogenate said highly unsaturated hydrocarbon to a less unsaturated hydrocarbon;
   wherein said treated catalyst composition is prepared by a process comprising contacting a catalyst composition comprising palladium with a first treating agent comprising carbon monoxide and a hydrogen-containing fluid under a first treating condition to provide said treated catalyst composition prior to contact thereof with said hydrocarbon-containing fluid; and
   wherein said first treating agent comprises a mole percentage of said carbon monoxide of at least about 0.0005 and no more than about 50.

2. A process according to claim 1 wherein said first treating agent further comprises an additional component selected from the group consisting of an inert gas, a hydrocarbon-containing gas, and combinations thereof.

3. A process according to claim 1 wherein said first treating condition comprises:
   a temperature wherein said temperature is at least about 50° F. and further wherein said temperature is no more than about 800° F.,
   a pressure wherein said pressure is at least about atmospheric and further wherein said pressure is no more than about 150 psia,
   a time period wherein said time period is at least about 0.1 hour and further wherein said time period is no more than about 50 hours, and
   a gas hourly space velocity wherein said gas hourly space velocity is at least about 1 liter of said first treating agent per liter of said catalyst composition per hour (liter/liter/hour) and further wherein said gas hourly space velocity is no more than about 50,000 liter/liter/hour.

4. A process according to claim 2 wherein said inert gas is nitrogen.

5. A process according to claim 1 wherein said process further comprises contacting said treated catalyst composition with a second treating agent comprising a hydrogen-containing fluid under a second treating condition.

6. A process according to claim 5 wherein said second treating agent further comprises an additional component selected from the group consisting of carbon monoxide, an inert gas, a hydrocarbon-containing gas, and combinations thereof.

7. A process according to claim 1 wherein said highly unsaturated hydrocarbon is selected from the group consisting of alkynes, diolefins, and combinations thereof.

8. A process according to claim 7 wherein said alkynes are selected from the group consisting of acetylene, propyne, 1-butyne, 2-butyne, 1-pentyne, 2-pentyne, 3-methyl-1-butyne, 1-hexyne, 1-heptyne, 1-octyne, 1-nonyne, 1-decyne, and combinations thereof.

9. A process according to claim 8 wherein said alkynes are acetylene and propyne.

10. A process according to claim 9 wherein said diolefins contain at least about 3 carbon atoms per molecule and no more than about 12 carbon atoms per molecule.

11. A process according to claim 10 wherein said diolefins are selected from the group consisting of propadiene, 1,2-butadiene, 1,3-butadiene, isoprene, 1,2-pentadiene, 1,3-pentadiene, 1,4-pentadiene, 1,2-hexadiene, 1,3-hexadiene, 1,4-hexadiene, 1,5-hexadiene, 2-methyl-1,2-pentadiene, 2,3-dimethyl-1,3-butadiene, heptadienes, methylhexadienes, octadienes, methylheptadienes, dimethylhexadienes, ethylhexadienes, trimethylpentadienes, methyloctadienes, dimethylheptadienes, ethyloctadienes, trimethylhexadienes, nonadienes, decadienes, undecadienes, dodecadienes, cyclopentadienes, cyclohexadienes, methylcyclopentadienes, cycloheptadienes, methylcyclohexadienes, dimethylcyclopentadienes, ethylcyclopentadienes, dicyclopentadiene, and combinations thereof.

12. A process according to claim 11 wherein said diolefins are selected from the group consisting of propadiene, 1,2-butadiene, 1,3-butadiene, pentadienes, cyclopentadienes, dicyclopentadiene, and combinations thereof.

13. A process according to claim 12 wherein said less unsaturated hydrocarbon is selected from the group consisting of ethylene, propylene, 1-butene, 2-butene, isobutylene, 1-pentene, 2-pentene, methyl-1-butenes, methyl-2-butenes, 1-hexene, 2-hexene, 3-hexene, methyl-1-pentenes, 2,3-dimethyl-1-butene, 1-heptene, 2-heptene, 3heptene, methyl-1-hexenes, methyl-2-hexenes, methyl-3-hexenes, dimethylpentenes, ethylpentenes, octenes, methylheptenes, dimethylhexenes, ethylhexenes, nonenes, methyloctenes, dimethylheptenes, ethylheptenes, trimethylhexenes, cyclopentene, cyclohexene, methylcyclopentene, cycloheptene, methylcyclohexene, dimethylcyclopentenes, ethylcyclopentenes, cyclooctenes, methylcycloheptenes, dimethylcyclohexenes, ethylcyclohexenes, trimethylcyclohexenes, methylcyclooctenes, dimethylcyclooctenes, ethylcyclooctenes, and combinations thereof.

14. A process according to claim 13 wherein said hydrocarbon-containing fluid further comprises a monoolefin.

15. A process according to claim 14 wherein said monoolefin is selected from the group consisting of ethylene, propylene, 1-butene, 2-butene, isobutylene, 1-pentene, 2-pentene, methyl-1-butenes, methyl-2-butenes, 1-hexene, 2-hexene, 3-hexene, methyl-1-pentenes, 2,3-dimethyl-1-butene, 1-heptene, 2-heptene, 3-heptene, methyl-1-hexenes, methyl-2-hexenes, methyl-3-hexenes, dimethylpentenes, ethylpentenes, octenes, methylheptenes, dimethylhexenes, ethylhexenes, nonenes, methyloctenes, dimethylheptenes, ethylheptenes, trimethylhexenes, cyclopentene, cyclohexene, methylcyclopentene, cycloheptene, methylcyclohexene, dimethylcyclopentenes, ethylcyclopentenes, cyclooctenes, methylcycloheptenes, dimethylcyclohexenes, ethylcyclohexenes, trimethylcyclohexenes, methylcyclooctenes, dimethylcyclooctenes, ethylcyclooctenes, and combinations thereof.

16. A process according to claim 15 wherein said hydrocarbon-containing fluid further comprises a saturated hydrocarbon selected from the group consisting of methane, ethane, propane, butane, methylpropane, methylbutane, dimethylbutane, pentanes, hexanes, and combinations thereof.

17. A process according to claim 16 wherein said hydrocarbon-containing fluid further comprises an aromatic hydrocarbon selected from the group consisting of benzene, toluene, ethylbenzene, styrene, xylenes, and combinations thereof.

18. A process according to claim 17 wherein said hydrogen is present in an amount of at least about 0.1 mole of hydrogen for each mole of said highly unsaturated hydrocarbon present in said hydrocarbon-containing fluid and further wherein said hydrocarbon-containing fluid comprises no more than about 1000 moles of hydrogen for each mole of said highly unsaturated hydrocarbon.

19. A process according to claim 18 wherein said hydrogenation condition comprises:
   a temperature wherein said temperature is at least about 50° F. and further wherein said temperature is no more than about 600° F.,
   a pressure wherein said pressure is at least about 15 psig and further wherein said pressure is no more than about 2000 psig, and
   a charge rate of said hydrocarbon-containing fluid to said hydrogenation zone such as to provide a gas hourly space velocity of at least about 1 liter of said hydrocarbon-containing fluid per liter of said treated catalyst composition per hour (liter/liter/hour) and further wherein said gas hourly space velocity is no more than about 50,000 liter/liter/hour.

20. A process comprising contacting a hydrocarbon-containing fluid which comprises a highly unsaturated hydrocarbon with a treated catalyst composition in the presence of hydrogen in a hydrogenation zone under a hydrogenation condition effective to hydrogenate said highly unsaturated hydrocarbon to a less unsaturated hydrocarbon;
   wherein said treated catalyst composition is prepared by a process comprising contacting a catalyst composition comprising palladium with a first treating agent comprising carbon monoxide under a first treating condition and with a second treating agent comprising a hydrogen-containing fluid under a second treating condition to provide said treated catalyst composition prior to contact thereof with said hydrocarbon-containing fluid.

* * * * *